United States Patent
Hirsch et al.

(10) Patent No.: US 9,566,078 B2
(45) Date of Patent: Feb. 14, 2017

(54) GUIDE SLEEVE FOR SUPRAPATELLAR SURGERY

(71) Applicant: Stryker European Holdings I, LLC, Kalamazoo, MI (US)

(72) Inventors: Oliver Hirsch, Kiel (DE); Claudia Graca, Kiel (DE); Ole Prien, Kiel (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 94 days.

(21) Appl. No.: 13/743,925

(22) Filed: Jan. 17, 2013

(65) Prior Publication Data

US 2013/0190570 A1    Jul. 25, 2013

(30) Foreign Application Priority Data

Jan. 19, 2012    (EP) .................................... 12000339

(51) Int. Cl.
*A61B 1/32*    (2006.01)
*A61B 17/17*    (2006.01)
(Continued)

(52) U.S. Cl.
CPC ........... *A61B 17/1767* (2013.01); *A61B 1/317* (2013.01); *A61B 1/32* (2013.01); *A61B 17/00234* (2013.01); *A61B 17/1677* (2013.01); *A61B 17/1697* (2013.01); *A61B 17/1764* (2013.01); *A61B 17/34* (2013.01); *A61B 17/56* (2013.01); *A61B 17/846* (2013.01); *A61B 17/1615* (2013.01); *A61B 17/1633* (2013.01);
(Continued)

(58) Field of Classification Search
CPC ........ A61B 17/1675–17/1677; A61B 17/1662; A61B 17/17; A61B 17/1764; A61B 17/1739; A61B 1/32

USPC ....... 600/201–212; 606/86 R, 87–89, 95–99, 606/104, 62–68

See application file for complete search history.

(56) References Cited

U.S. PATENT DOCUMENTS 2,181,746 A    11/1939    Siebrandt
2,969,162 A *   1/1961    Stutske .................. H01J 29/87
                                                        220/2.1 A
(Continued)

FOREIGN PATENT DOCUMENTS

CH        396304 A    7/1965
CH        668692 A5   1/1989
(Continued)

OTHER PUBLICATIONS

Althausen et al., Journal of Orthopaedic Trauma, vol. 16, No. 10, 687-690, 2002.
(Continued)

*Primary Examiner* — Eduardo C Robert
*Assistant Examiner* — Michelle C Eckman
(74) *Attorney, Agent, or Firm* — Lerner, David, Littenberg, Krumholz & Mentlik, LLP

(57) ABSTRACT

A tissue protection sleeve for use in suprapatellar surgery is provided. The sleeve has a first end, a second end, an inner surface and an outer surface. The sleeve further comprises at least two open grooves that extend along the inner surface from the first end to the second end. The grooves are adapted to accommodate elongated fixation elements inserted into a tibia. A drill guide sleeve and a trocar for inserting a guide wire are also provided and can be accommodated by the tissue protection sleeve.

16 Claims, 7 Drawing Sheets

(51) Int. Cl.

| | | |
|---|---|---|
| *A61B 1/317* | (2006.01) | |
| *A61B 17/16* | (2006.01) | |
| *A61B 17/56* | (2006.01) | |
| *A61B 17/84* | (2006.01) | |
| *A61B 17/34* | (2006.01) | |
| *A61B 17/00* | (2006.01) | |
| *A61B 17/02* | (2006.01) | |

(52) U.S. Cl.
CPC ....... *A61B 17/1675* (2013.01); *A61B 17/3431* (2013.01); *A61B 2017/00862* (2013.01); *A61B 2017/0268* (2013.01)

(56) References Cited

U.S. PATENT DOCUMENTS

| | | | |
|---|---|---|---|
| 3,867,932 A | 2/1975 | Huene | |
| 4,237,875 A | 12/1980 | Termanini | |
| 4,441,492 A | 4/1984 | Rydell et al. | |
| 4,449,532 A | 5/1984 | Storz | |
| 4,498,468 A | 2/1985 | Hansson | |
| 4,545,374 A * | 10/1985 | Jacobson | 600/210 |
| 4,549,538 A | 10/1985 | Schadrack, III et al. | |
| 4,616,638 A | 10/1986 | Griggs | |
| 4,621,628 A | 11/1986 | Brudermann | |
| 4,699,611 A | 10/1987 | Bowden | |
| 4,872,451 A | 10/1989 | Moore et al. | |
| 4,917,111 A | 4/1990 | Pennig et al. | |
| 4,959,538 A | 9/1990 | Swart | |
| 4,969,889 A | 11/1990 | Greig | |
| 5,147,367 A | 9/1992 | Ellis | |
| 5,160,323 A | 11/1992 | Andrew | |
| 5,207,753 A | 5/1993 | Badrinath | |
| 5,429,641 A | 7/1995 | Gotfried | |
| 5,431,676 A | 7/1995 | Dubrul et al. | |
| 5,458,600 A | 10/1995 | Stapert et al. | |
| 5,601,550 A | 2/1997 | Esser | |
| 5,624,447 A | 4/1997 | Myers | |
| 5,683,400 A * | 11/1997 | McGuire | 606/96 |
| 5,779,705 A | 7/1998 | Matthews | |
| 5,938,686 A | 8/1999 | Benderev et al. | |
| 5,951,561 A | 9/1999 | Pepper et al. | |
| 6,010,505 A | 1/2000 | Asche et al. | |
| 6,033,407 A * | 3/2000 | Behrens | 606/62 |
| 6,063,088 A * | 5/2000 | Winslow | 606/86 A |
| 6,120,504 A | 9/2000 | Brumback et al. | |
| 6,120,511 A | 9/2000 | Chan | |
| 6,206,880 B1 | 3/2001 | Karladani | |
| 6,270,499 B1 | 8/2001 | Leu et al. | |
| 6,402,753 B1 | 6/2002 | Cole et al. | |
| 7,033,363 B2 | 4/2006 | Powell | |
| 7,090,677 B2 | 8/2006 | Fallin et al. | |
| RE39,995 E | 1/2008 | Pepper et al. | |
| 7,422,594 B2 | 9/2008 | Zander | |
| 7,476,225 B2 | 1/2009 | Cole | |
| 7,819,877 B2 | 10/2010 | Guzman et al. | |
| 7,927,336 B2 | 4/2011 | Rasmussen | |
| 7,981,114 B2 | 7/2011 | Zander | |
| 8,147,492 B2 | 4/2012 | Justin et al. | |
| 8,202,216 B2 * | 6/2012 | Melkent et al. | 600/215 |
| 8,328,805 B2 | 12/2012 | Cole | |
| 8,360,970 B2 * | 1/2013 | Mangiardi | 600/210 |
| 2002/0133156 A1 | 9/2002 | Cole | |
| 2003/0018340 A1 * | 1/2003 | Branch | A61B 17/88 606/96 |
| 2004/0243138 A1 | 12/2004 | Cole | |
| 2006/0155290 A1 * | 7/2006 | Shino | 606/86 |
| 2006/0190001 A1 * | 8/2006 | Powell | 606/96 |
| 2006/0229730 A1 * | 10/2006 | Railey et al. | 623/21.18 |
| 2007/0100342 A1 | 5/2007 | Green et al. | |
| 2007/0118119 A1 | 5/2007 | Hestad | |
| 2007/0225568 A1 * | 9/2007 | Colleran | A61B 1/32 600/201 |
| 2007/0255282 A1 * | 11/2007 | Simonton et al. | 606/60 |
| 2008/0086144 A1 * | 4/2008 | Zander | 606/96 |
| 2008/0132900 A1 * | 6/2008 | Prien | A61B 17/1728 606/96 |
| 2008/0183171 A1 | 7/2008 | Elghazaly et al. | |
| 2008/0208261 A1 | 8/2008 | Medoff | |
| 2008/0221394 A1 * | 9/2008 | Melkent et al. | 600/201 |
| 2008/0269748 A1 | 10/2008 | Justin et al. | |
| 2008/0269749 A1 | 10/2008 | Shalaby et al. | |
| 2008/0269750 A1 | 10/2008 | Justin | |
| 2008/0269751 A1 | 10/2008 | Matityahu | |
| 2008/0287950 A1 | 11/2008 | Frigg et al. | |
| 2008/0294164 A1 | 11/2008 | Frank et al. | |
| 2009/0036746 A1 * | 2/2009 | Blackwell et al. | 600/219 |
| 2009/0043309 A1 | 2/2009 | Rasmussen | |
| 2009/0043310 A1 | 2/2009 | Rasmussen | |
| 2009/0088761 A1 * | 4/2009 | Roose et al. | 606/87 |
| 2009/0112268 A1 | 4/2009 | Cole | |
| 2009/0138044 A1 * | 5/2009 | Bergeron et al. | 606/246 |
| 2009/0299372 A1 * | 12/2009 | Steiner et al. | 606/79 |
| 2010/0022844 A1 * | 1/2010 | Mangiardi | A61B 17/025 600/201 |
| 2010/0042104 A1 * | 2/2010 | Kota et al. | 606/79 |
| 2010/0121339 A1 * | 5/2010 | Whittaker et al. | 606/98 |
| 2010/0241121 A1 | 9/2010 | Logan et al. | |
| 2011/0213375 A1 * | 9/2011 | Sikora et al. | 606/87 |
| 2012/0010659 A1 * | 1/2012 | Angert et al. | 606/247 |
| 2013/0023891 A1 * | 1/2013 | Berberich et al. | 606/98 |
| 2013/0079783 A1 * | 3/2013 | Bertagnoli et al. | 606/87 |
| 2013/0172890 A1 * | 7/2013 | Limouze et al. | 606/62 |
| 2013/0178860 A1 * | 7/2013 | Dorawa et al. | 606/96 |
| 2014/0031874 A1 * | 1/2014 | Kucharzyk et al. | 606/279 |
| 2014/0039264 A1 * | 2/2014 | Heiman | 600/202 |
| 2014/0221760 A1 * | 8/2014 | Perrow | 600/210 |

FOREIGN PATENT DOCUMENTS

| | | |
|---|---|---|
| DE | 19708279 A1 | 9/1998 |
| DE | 10309987 A1 | 9/2004 |
| DE | 102008004922 A1 | 7/2009 |
| EP | 0273872 A1 | 7/1988 |
| EP | 0361641 A1 | 4/1990 |
| EP | 0518071 A1 | 12/1992 |
| EP | 0 550 814 A2 | 7/1993 |
| EP | 0623006 A1 | 11/1994 |
| EP | 0633748 A1 | 1/1995 |
| EP | 0712607 A2 | 5/1996 |
| EP | 0882431 A1 | 12/1998 |
| EP | 1124492 A1 | 8/2001 |
| EP | 1285630 A1 | 2/2003 |
| EP | 1488746 A1 | 12/2004 |
| RU | 2152188 C1 | 7/2000 |
| WO | 02067811 A2 | 9/2002 |
| WO | 03015650 A1 | 2/2003 |
| WO | 2006040508 A1 | 4/2006 |

OTHER PUBLICATIONS

Anup et al., Journal of Orthopaedic Surgery, 10(1): 17-21, 2002.
Biomet, Percutaneous Lateral Suprapatellar Approach in a Semi-extended Position, Mar. 18, 2010.
Clinical Trials.gov, Suprapatellar Versus Infrapateller Nailing in Tibial Fractures: A Pilot Study, 4 pages, printed May 31, 2011.
Cole, Techniques in Orthopaedics, 13(1):27-37, 1998.
DePuy, Tibial Nailing System , Surgical Technique, 2004.
Devitt et al., International Orthopaedics, SICOT, pp. 92-96, 1998.
European Search Report, EP12000339.7, dated Oct. 22, 2012.
Hak, Trauma Update, Orthopedics, OrthoSupersite.com, pp. 532-535, Jun. 24, 2011.
Jakma et al., Acta Orthop. Belg., 77, pp. 834-837, 2011.
Karladani et al., Injury, Int. J Care Injured, 32, pp. 736-739, 2001.
Morandi et al., Healio Orthopedics, Orthopedics, vol. 33, Issue 3, Orthopedics Mar. 2010.
Russell et al., Trigen IM Nail System, Surgical Technique Mar. 1998.
Smith & Nephew, Trigen Meta-Nail, Jun. 2009.
Stryker T2 Tibial Nailing System, Operative Technique, 2010.
Synthes, Suprapatellar Instrumentation for Expert Tibial Nail, Technique Guide, May 2012.

(56) References Cited

OTHER PUBLICATIONS

Toivanen et al., Journal of Bone and Joint Surgery, Vo. 84-A, No. 4, pp. 580-585, Apr. 2002.
Tornetta et al., Clinical rthopaedics and Related Research, No. 328, pp. 185-189, 1996.
Zimmer, Natural Nail System, Surgical Technique, pp. 1-7, date not known.

* cited by examiner

GUIDE SLEEVE FOR SUPRAPATELLAR SURGERY

CROSS-REFERENCE TO RELATED APPLICATION

The present application claims priority from European Patent Application No. 12000339.7 filed Jan. 19, 2012, the disclosure of which is hereby incorporated herein by reference.

BACKGROUND OF THE INVENTION

The present disclosure generally relates to surgical instruments for use in surgical procedures. In particular, a sleeve suitable for suprapatellar surgery and a system comprising the sleeve are described.

When treating a tibial fracture (e.g., for realigning the tibia), a patient's knee is typically flexed approximately 90° in order for the surgeon to get access to the top of the tibia in front of the patella for inserting an implant such as an intramedullary nail for fracture fixation. However, patients report frequently on high rates of anterior knee pain caused by the common infrapatellar nailing procedure.

A so-called suprapatellar approach for intramedullary nailing of tibial fractures may be used by surgeons, since it provides first evidence of reduced anterior knee pain and thus enhanced clinical outcome. During suprapatellar surgery, a drill sleeve is inserted between the patella and the femur of the patient's knee and the necessary flexion of the knee joint may consequently be significantly less than 90°. Nonetheless, as suprapatellar surgery is performed through a, supposedly, healthy joint (patellofemoral joint), the joint surfaces need to be protected during the surgery.

DE 10 2008 004 922 A1 discloses a device for bone surgery close to a joint of the bone. The device comprises a sleeve with a central opening and a cylinder with a plurality of canals for insertion of wires. The cylinder is adapted to enclose the sleeve.

It has been found that the device of DE 10 2008 004 922 A1 is over-dimensioned for suprapatellar surgery. If all dimensions of the device were proportionally decreased, the maximum size of a drill (and an implant) that need to be introduced through the device would be compromised at the cost of an inferior recovery procedure.

It has further been found that the presence of canals inside the cylinder walls complicates cleaning and sterilization of the cylinder. This complication is due to the fact that tissue debris may adhere to the inner surfaces of the canals. Additionally, anterior displacement of the cylinder is likely to occur which can lead to unnecessary iatrogenic injuries.

Instruments for use in tibial nailing are shown in U.S. Pat. Nos. 7,476,225 and 8,328,805.

BRIEF SUMMARY OF THE INVENTION

Accordingly, there is a need a for a sleeve suitable for suprapatellar surgery which enables the use of drills and implants of sufficient size and which facilitates cleaning and sterilization.

According to one aspect, a sleeve which has a longitudinal axis is provided, wherein the sleeve comprises a first end, a second end, an inner surface, an outer surface and at least two grooves that extend at the inner surface from the first end to the second end, and wherein the grooves are adapted to accommodate elongated fixation elements. The elongated fixation elements may, for example, be realized as wires (e.g., so-called K-wires), nails or pins.

The sleeve may function or be used as a guiding sleeve for guiding another component towards a surgical field. It may be used for suprapatellar surgery or other surgical operations.

The sleeve may be made of a rigid material. This rigid material may be a metal or a hard plastic material.

Alternatively, the sleeve may be made of an elastic material. The elastic material may be advantageous from the perspective of protecting the patella-femoral (or any other) joint. A sleeve made of an elastic material may permit a wrenching or rotation of the sleeve along the longitudinal axis of the sleeve. Furthermore, a sleeve made of an elastic material may permit a bending along the longitudinal axis of the sleeve. This sleeve may be made from PEEK, ultra-high molecular weight polyethylene, thermoplastic polyurethane (TPU) or combinations thereof.

The sleeve may have portions along the longitudinal axis where the outer surface adjacent to the at least two grooves projects radially. Such portions have the appearance of ribs. The portions may extend along more than the half of the length of the sleeve. For example, the ribs may extend along at least two thirds of the length of the sleeve.

According to one embodiment, the inner sleeve surface is substantially circular along a circumference between the grooves. The outer surface along a circumference between the grooves may also be substantially circular. In this case, the inner surface and the outer surface may be concentric. Furthermore, the outer surface adjacent to the grooves may be circular and concentric with each respective groove. As an example, the outer surface may have ribs along the grooves in the inner surface.

The sleeve may have a uniform thickness along the entire circumference. In such an embodiment, the thickness between the inner surface and the outer surface along the circumference between the grooves may be the same as the thickness between the grooves and the outer surface adjacent to the grooves. Furthermore, the first end of the sleeve may have a flat surface perpendicular to the longitudinal axis of the sleeve.

The grooves may be parallel with the longitudinal axis of the sleeve. Alternatively, the grooves may be inclined relative to the longitudinal axis of the sleeve. The angle of the inclination between the grooves and the longitudinal axis of the sleeve may be 20° or less. Furthermore, the grooves may be inclined concentrically towards the second end of the sleeve. The grooves may thus be inclined in such a way that the distance between the grooves in a radial direction is smaller at the second distal end of the sleeve than at the first or proximal end of the sleeve.

The sleeve may comprise two grooves located substantially at opposite sides along the circumference of the inner surface. The two (or more) grooves may alternatively have an angular distance relative to the longitudinal direction of less than 180°. The angular distance between the grooves of the inner surface may, for example, be less than 150°. As an example, the sleeve may comprise three grooves along the circumference of the inner surface. Moreover, the guiding sleeve may comprise four grooves along the circumference of the inner surface. In such a realization, the four grooves may be equally displaced at an angular distance of 90° along the circumference of the inner surface.

The sleeve may comprise a gripping portion radially and outwardly protruding from the first end of the sleeve. The gripping portion may constitute an end cap of the sleeves. The gripping portion may be asymmetric and protrude only in one direction. Alternatively, the gripping portion may protrude radially in more than one direction. The gripping portion may be provided with a surface structure to provide a better grip.

The outer surface of the sleeve may have a chamfered portion at the second end. The chamfered portion may be arranged at an angle of approximately 45° in relation to the longitudinal axis of the sleeve. The chamfered portion may extend along the entire circumference of the second end.

The inner surface of the sleeve may be conical with its larger diameter side proximate to the first end and its smaller diameter side proximate to the second end. Alternatively, the inner surface may have a conical portion and a cylindrical portion, wherein the larger diameter side of the conical portion is located proximate to the first end, the cylindrical portion extends from the smaller diameter side of the conical portion to the second end and the smaller diameter side of the conical portion has substantially the same diameter as the cylindrical portion. The conical portion may extend in a longitudinal direction of the sleeve along about 25% of the length of the sleeve and the cylindrical portion may extend in a longitudinal direction of the sleeve along about 75% of the length of the sleeve.

According to a further aspect, there is provided a sleeve configured for use in suprapatellar surgery, wherein the sleeve is made of an elastic material.

According to a still further aspect, there is provided a system comprising the sleeve as presented herein and a drill sleeve. The drill sleeve may be adapted to be inserted into the sleeve. An outer surface of the drill sleeve may substantially match the inner surface of the sleeve. Canals for guiding the fixation elements may be defined between the grooves and the outer surface of the drill sleeve.

The drill sleeve may comprise a portion with an enlarged diameter at a first end of the drill sleeve. The portion with an enlarged diameter may comprise at least two openings at an end facing a second end of the drill sleeve. The at least two openings may be adapted to mate (e.g., align) with the at least two grooves of the sleeve when the drill sleeve is inserted into the sleeve.

The enlarged diameter portion of the drill sleeve and the outer surface of the first end of the sleeve may be circular and have the same diameter. In the case where the sleeve has a radially and outwardly protruding gripping portion at its first end, the drill sleeve may or may not have a corresponding gripping portion.

The at least two openings of the drill sleeve may be inclined relative to the longitudinal axis of the drill sleeve. The angle of the inclination between the openings and a longitudinal axis of the drill sleeve may be 20° or less. Furthermore, the openings may be inclined towards the second end of the drill sleeve. The openings may be inclined in such a way that the distances between the openings along a circumferential direction are shorter closer to the second end of the drill sleeve than at the first end of the drill sleeve. The at least two openings may extend from a first end adjacent to a first end of the drill sleeve to the second end of the portion with an enlarged diameter. The at least two openings may be bores.

The sleeve and the drill sleeve may be adapted to be rotationally locked relative to each other. The sleeve and the drill sleeve may be locked by a protrusion and a recess in the longitudinal direction of the sleeve and the drill sleeve, respectively. One or more protrusions may be arranged at a flat surface of the first end of the sleeve and one or more corresponding recesses may be arranged at the portion of the drill sleeve having an enlarged diameter, or vice versa.

The drill sleeve may comprise a recess at the circumference of the portion with an enlarged diameter. The recess may be an opening from the outer surface of the enlarged diameter portion perpendicular to the longitudinal axis of the drill sleeve. The end of the opening may be located outside the inner surface of the drill sleeve. Alternatively, the opening may protrude from the outside of the enlarged diameter portion of the drill sleeve through the inner surface of the drill sleeve. The recess may be a bore.

According to a further realization, the system may comprise at least two fixation elements. The fixation elements may, for example, be wires (such as K-wires), nails or pins.

According to a further realization, the system may comprise a device adapted to engage at least one of the sleeve and the drill sleeve for positioning either one or both of them. The device may comprise a shaft, a handle connected to one end of the shaft and a sleeve holder connected to the opposite end of the shaft. The sleeve holder may define a space in which at least one of the sleeve and the drill sleeve is to be positioned. A locking element may be movable along the shaft. The locking element may be adapted to protrude into the space of the sleeve holder. A control portion may be connected to the locking element for retracting the locking element out from the space of the sleeve holder.

According to a further realization, the system may further comprise a trocar adapted to be inserted into the drill sleeve. The trocar may have a locking element adapted to lock the trocar against (e.g., rotational and/or translational) movement relative to the drill sleeve.

A method for suprapatellar surgery is provided also. The method comprises providing a system as presented herein, and inserting at least two fixation elements towards the tibia through the at least two grooves of the sleeve, wherein the at least two grooves are closed at their open sides by an outer surface of the drill sleeve.

BRIEF DESCRIPTION OF THE DRAWINGS

Further details, advantages and aspects of the present disclosure will become apparent from the following embodiments taking in conjunction with the drawings, wherein.

DETAILED DESCRIPTION

Figure 1:
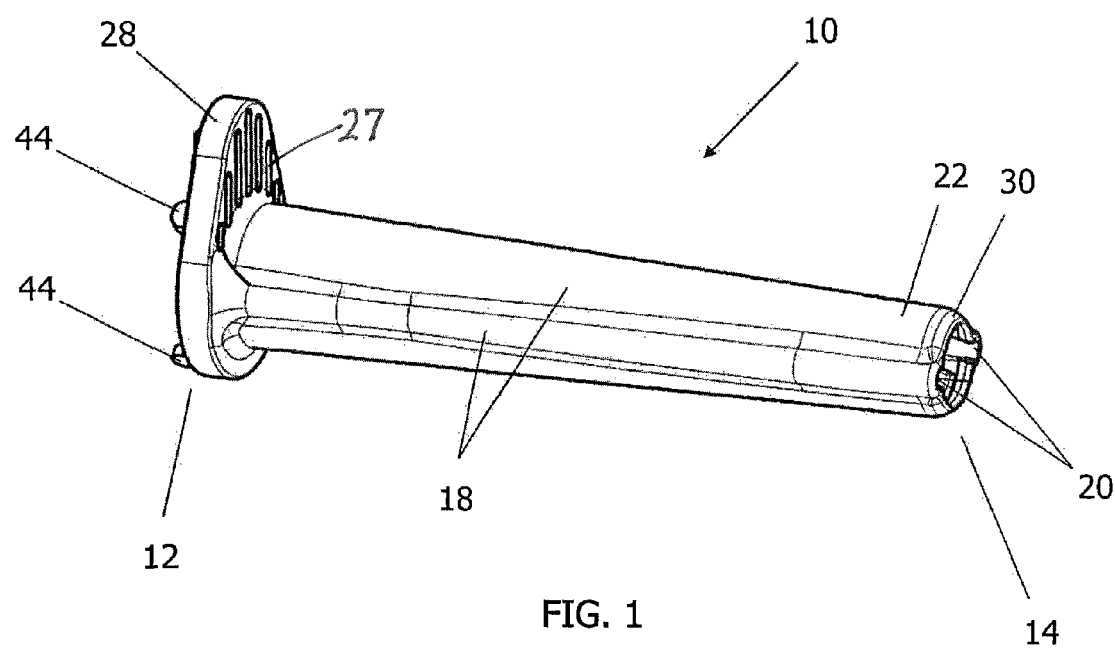
FIG. 1 shows a perspective view of an embodiment of a sleeve suitable for suprapatellar surgery.

In the following, several embodiments of a sleeve and a system comprising the sleeve suitable for suprapatellar surgery will be described. The same reference numerals will be used to denote the same or similar structural features of the sleeve and the system with the sleeve. It will be appreciated that the sleeve and the system could also be used for other surgical procedures.

FIG. 1 shows a perspective view of an embodiment of a sleeve 10. The sleeve 10 is, in the present embodiment, made from an elastic material so as to protect the tissue or cartilage into which the sleeve is to be introduced. The sleeve 10 may also be referred to as a guiding sleeve since it is adapted to guide a drill sleeve and fixation elements as described below.

As shown in FIG. 1, the sleeve 10 has a first or proximal end 12 that will during surgery face away from a tibia and a second or distal end 14 that will be directed towards the tibia. The sleeve 10 inner surface has two grooves 20 extending from the first end 12 to the second end 14. The two grooves 20 are adapted to guide and accommodate elongate fixation elements (not shown) during suprapatellar surgery as will be described in greater detail below.

An angular distance between the grooves 20 along the circumference of the sleeve 10 is approximately 180°. The two grooves 20 extend substantially parallel with a longitudinal axis of the sleeve 10 at a slight inclination relative to the longitudinal axis such that the radial distance at the first end 12 is larger than at the second end 14.

The sleeve 10 has an outer surface 18. The outer surface 18 has two circular portions 22 along a circumferential direction of the sleeve 10 between the two grooves 20. Close to the second end 14, the outer surface 18 adjacent to the grooves 20 extends outside the circular portion 22, i.e. the outer surface 18 adjacent to the grooves 20 projects radially outwardly in the form of two ribs. Close to the first end 12, the circular portion 22 of the outer surface 18 extends outside the outer surface 18 adjacent to the grooves 20.

The sleeve 10 comprises at its first end 12 a gripping portion 28. The gripping portion 28 is configured to comprise a radially outwardly protruding tab or flange. The gripping portion 28 has also a circular section which is concentric relative to the circular portion 22. The gripping portion 28 is provided with a plurality of protrusions 44 extending along the longitudinal axis of the sleeve 10. In the view of FIG. 1, only two of the protrusions 44 are visible.

Moreover, the sleeve 10 is provided with a chamfered portion 30 at second end 14. The chamfered portion 30 extends along the entire circumference of the second end 14 of the sleeve 10 and facilitates insertion of the sleeve 10 in the patient's joint.

Figures 2, 3:
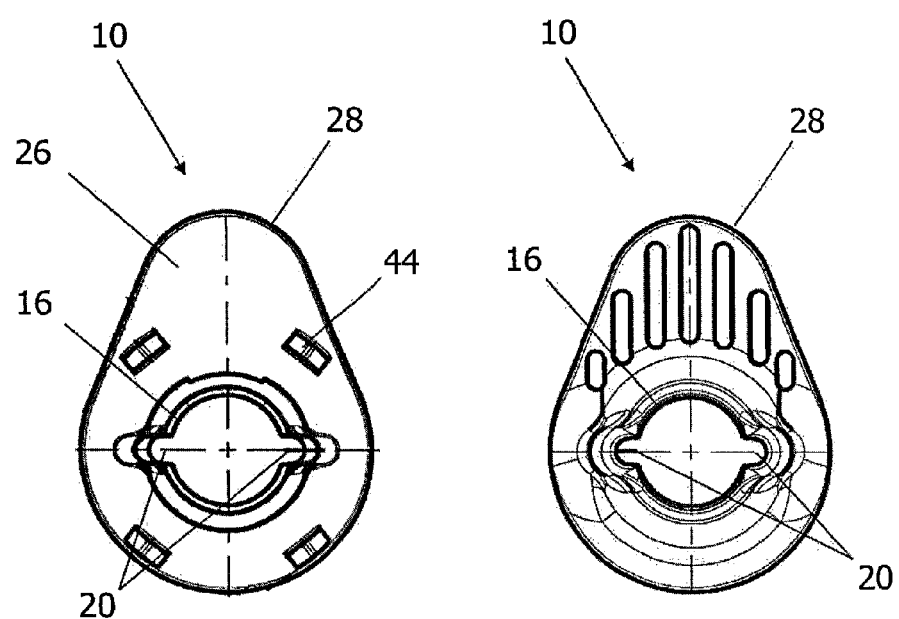
FIG. 2 shows a top view of the sleeve of FIG. 1.
FIG. 3 shows a bottom view of the sleeve of FIG. 1.

FIG. 2 illustrates a top view of the sleeve 10 as seen from the first end 12. The sleeve 10 has an inner surface denoted by 16. The inner surface 16 is here illustrated as substantially circular along its circumference between the grooves 20. The gripping portion 28 has a flat surface 26 on its top. The flat surface 26 extends perpendicularly to the longitudinal axis 24 of the sleeve 10. The grooves 20 are here illustrated as having a curved bottom with a circumference of approximately 180°. In the view of FIG. 2, the four proximally extending protrusions 44 can be seen.

FIG. 3 shows a bottom view of the sleeve 10 as seen from the second end 14. The radially outwardly protruding tab of the gripping portion 28 is provided with grooves 27 to provide a better grip.

Figure 4:
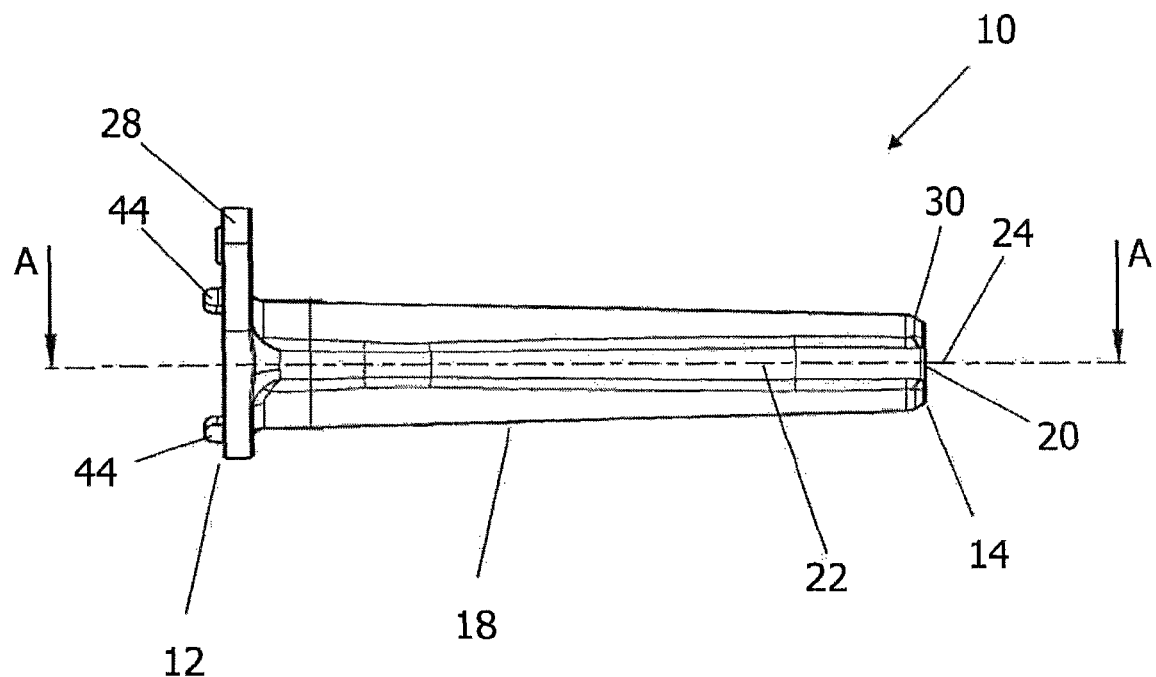
FIG. 4 shows a side view of the sleeve of FIG. 1.

FIG. 4 shows a side view of the sleeve 10. As becomes apparent from FIG. 4, the outer surface 18 between the grooves 20 has a conical form with its larger diameter portion close to the gripping portion 28 and its smaller diameter portion close to the chamfered portion 30. Line A-A extends along the longitudinal axis of the sleeve 10 and is also denoted by 24. Line A-A is concentric with the inner surface 16 between the grooves 20.

Figure 5:
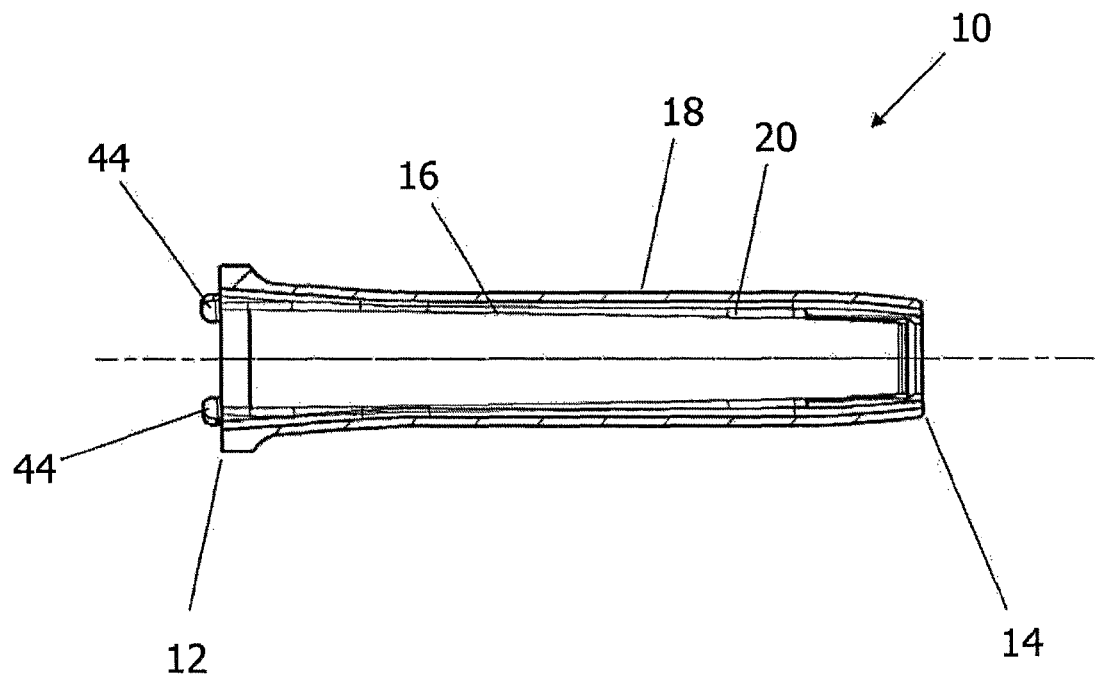
FIG. 5 shows a cross section of the sleeve along line A-A of FIG. 4.

FIG. 5 shows a cross section along line A-A of FIG. 4. In this view, it can be seen that the diameter of the outer surface 18 close to the grooves 20 at the second end 14 is larger than the diameter of the outer surface 18 between the grooves 20 at the second end 14 (as illustrated in FIG. 4).

Figure 6:
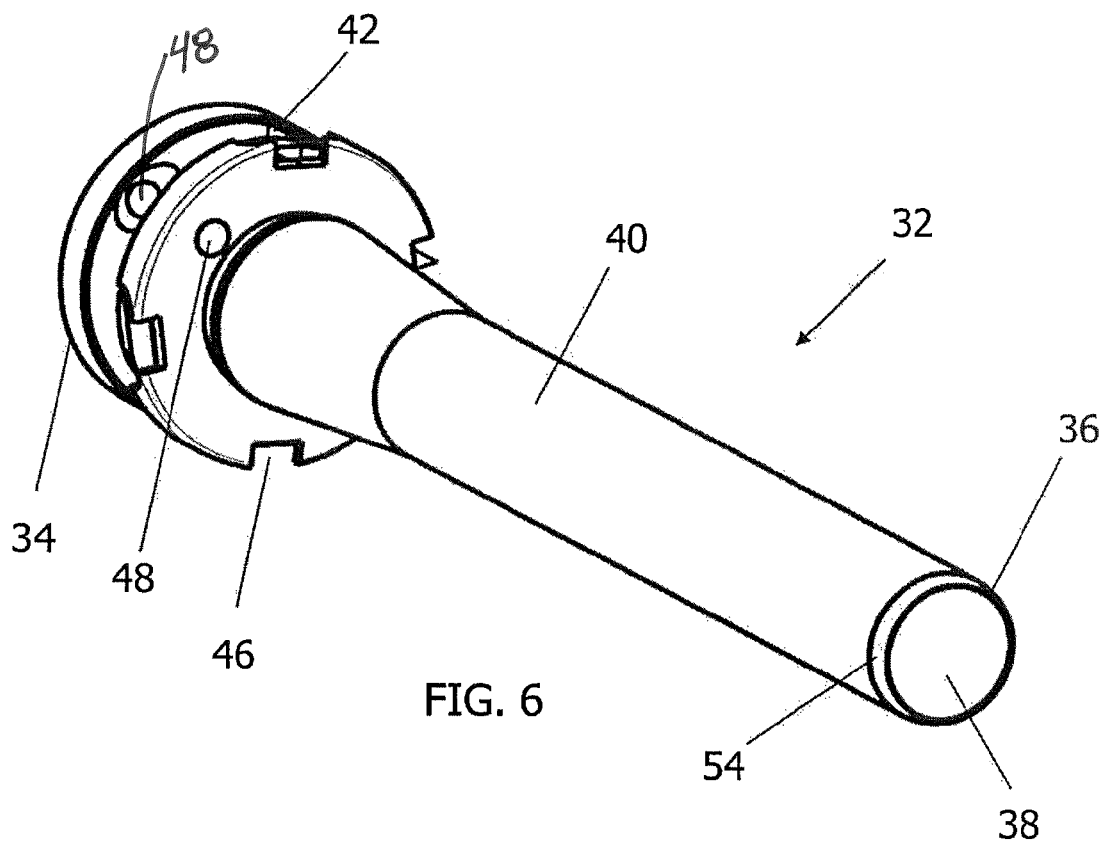
FIG. 6 shows a perspective view of an embodiment of a drill sleeve.

FIG. 6 shows a perspective view of a drill sleeve 32 adapted to be inserted into the sleeve 10. The drill sleeve 32 has a first or proximal end 34 that during surgery faces away from the tibia and a second end 36 facing towards the tibia. At the first end 34 the drill sleeve 32 has a portion 42 with an enlarged diameter. In the portion 42, two openings 48 in the form of through-bores are provided. One opening 48 can be seen in the view of FIG. 6.

The drill sleeve 32 has a chamfered portion 54 at its second or distal end 36. The drill sleeve 32 has an outer surface 40 between the portion 42 with an enlarged diameter and the chamfered portion 54. An inner surface or bore 38 of the drill sleeve 32 can be seen through an opening at the second end 36 of the drill sleeve 32. The inner surface 38 has a circular cross-section.

Figure 7:
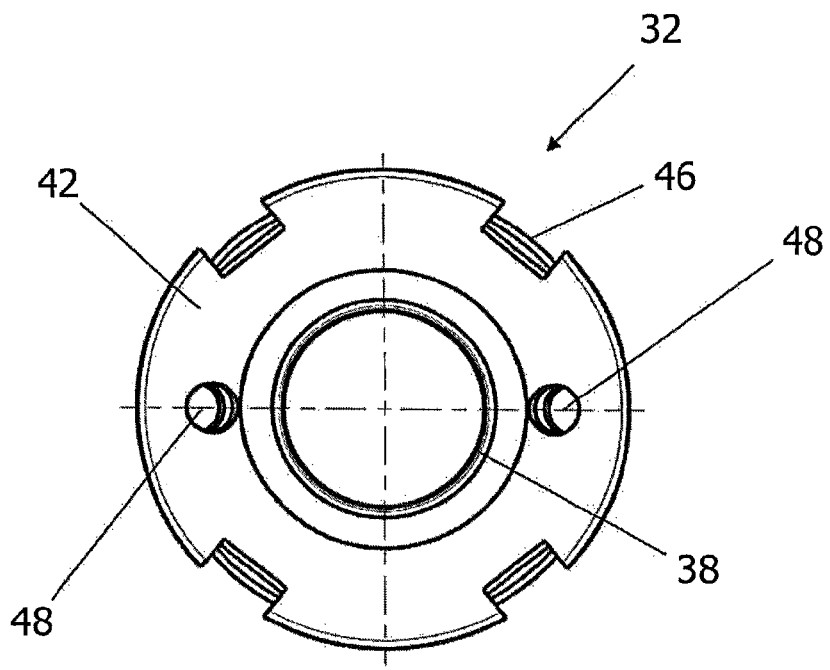
FIG. 7 shows a bottom view of the drill sleeve of FIG. 6.

FIG. 7 shows a bottom view of the drill sleeve 32 as seen from the second end 36. Here, both openings 48 can be seen. The openings 48 are located at opposite sides relative to a circumference of the inner surface 38. The openings 48 have axes that are slightly inclined relative to the longitudinal axis of the drill sleeve 32. The distance between the openings 48 along a circumferential direction at the first end 34 is larger than the distance between the openings 48 along a circumferential direction at the distal part of the enlarged diameter portion 42 facing the second end 36. Four recesses 46 are arranged along the circumference of the portion 42. The recesses 46 are dimensioned to accommodate the protrusions 44 of the sleeve 10 (see FIG. 2).

Figure 8:
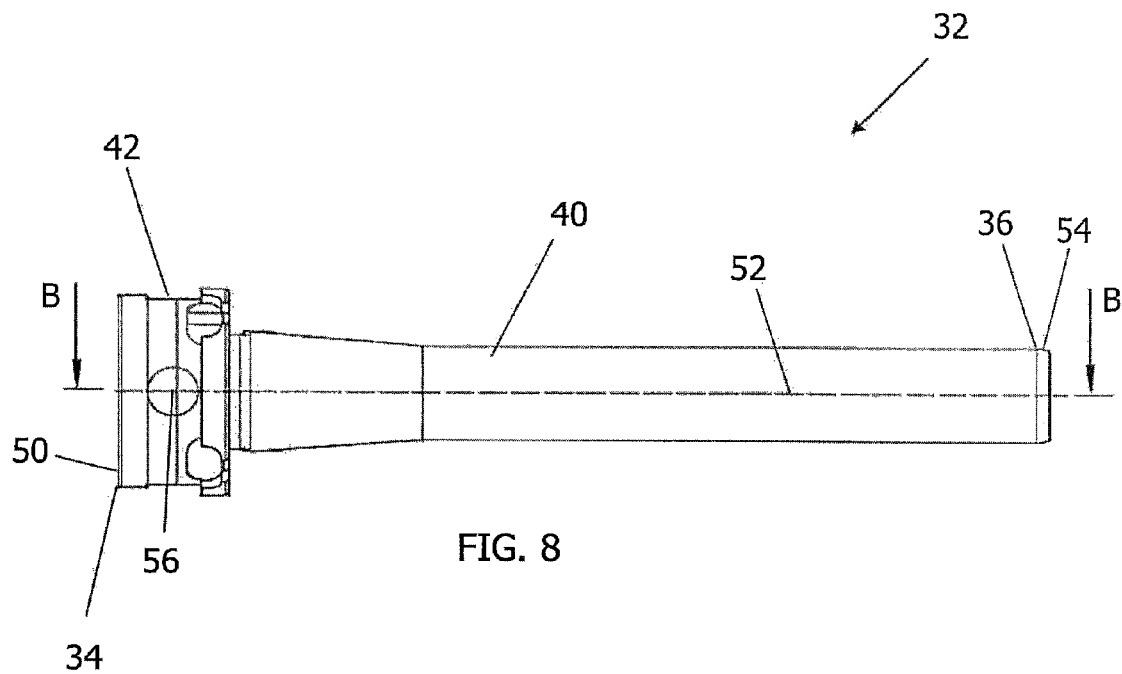
FIG. 8 shows a side view of the drill sleeve of FIG. 6.

FIG. 8 shows a side view of the drill sleeve 32. As shown in FIG. 8, a circular recess 56 is arranged at the portion 42 having an enlarged diameter. The recess 56 is here illustrated as a circular opening protruding through the portion 42 into the inner bore 38. The recess 56 extends perpendicularly to the longitudinal axis of the drill sleeve 32.

With reference to FIG. 8, the outer surface 40 of the drill sleeve 32 has a tubular part 41 and a conical part 43. The conical part has its larger diameter portion close to the portion 42 i.e., at the proximal end of sleeve 32, and its smaller diameter part adjacent the tubular part 41. Line B-B extends along the longitudinal axis of the drill sleeve 32 and is concentric with the inner surface 38 of the drill sleeve 32. Line B-B is also denoted as 52. The drill sleeve 32 has a flat proximal surface 50 extending perpendicularly to longitudinal axis 52 of drill sleeve 32 at first end 34.

Figure 9:
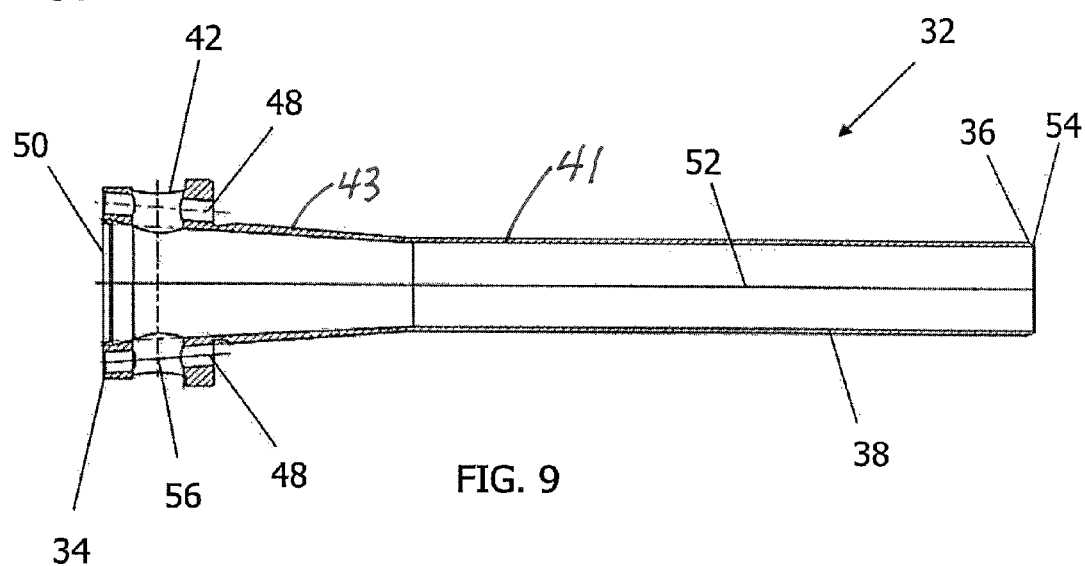
FIG. 9 shows a cross section of a drill sleeve along line B-B of FIG. 8.

FIG. 9 shows a cross section along line B-B of FIG. 8. Like the outer surface 40, the inner surface 38 has a tubular part and a conical part. The conical part has its larger diameter side at the first end 34 and its smaller diameter side adjacent to the tubular part. The conical part has a substantially uniform thickness between the chamfered portion 54 and the portion 42 having an enlarged diameter. The axes of the openings 48 are parallel with the outer surface 40 of the conical part 43 of the drill sleeve 32.

Figure 10:
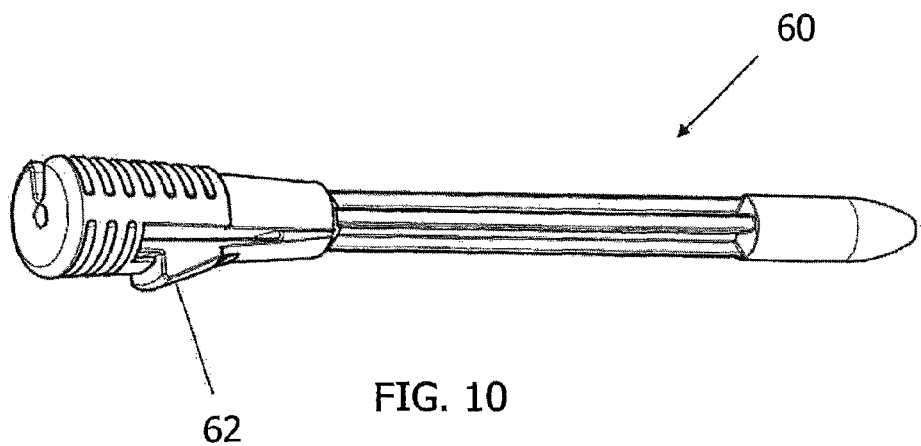
FIG. 10 shows a perspective view of an embodiment of a trocar.

FIG. 10 shows a perspective view of a trocar 60 for insertion into the drill sleeve 32. The trocar 60 has a locking element 62. The locking element 62 is flexible in a radial direction of the trocar 60 and has a radially outwardly protruding part. The trocar 60 is adapted to be locked relative to the drill sleeve 32 by the locking element 62. The trocar 60 has a central opening or cannulation along a longitudinal axis of the trocar 60. This cannulation can be used for a guide wire.

Figure 11:
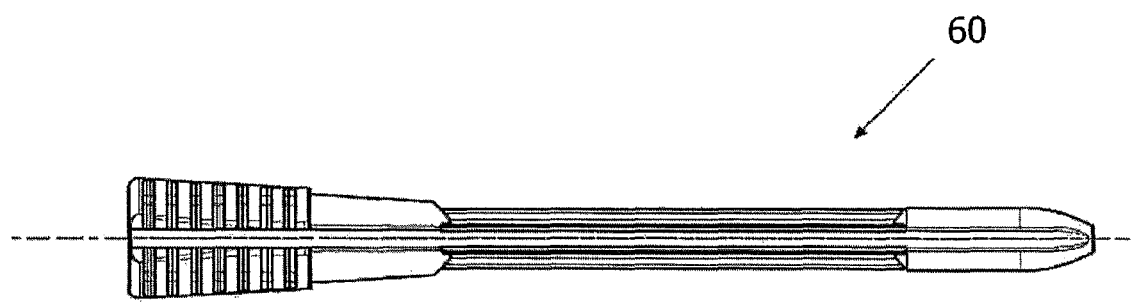
FIG. 11 shows a side view of the trocar of FIG. 10.

FIG. 11 shows a side view of the trocar 60. As shown in FIG. 11, the trocar 60 has a conical portion at its proximal end facing the femur and a sharp portion at its distal end facing the tibia.

Figure 12:
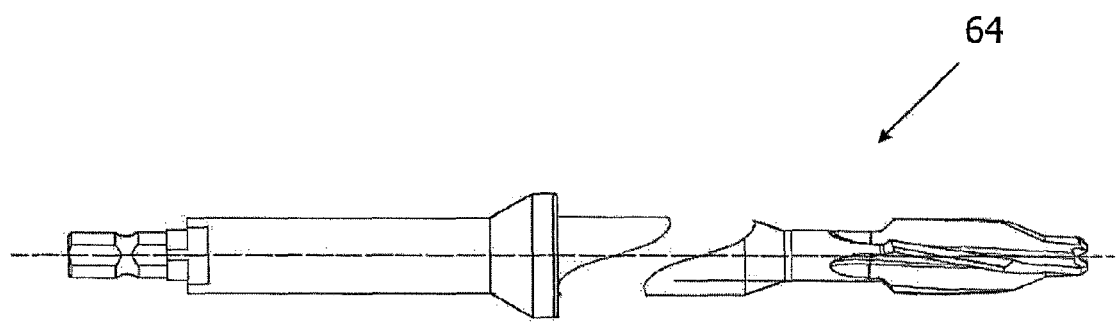
FIG. 12 shows a side view of an embodiment of a drill.

FIG. 12 shows a side view of a drill 64 for insertion into the drill sleeve 32. The drill 64 is adapted to be operated at least partly through the drill sleeve 32 when the trocar 60 is removed from the drill sleeve 32. The drill 64 may be cannulated to receive a guide wire.

Figure 13:
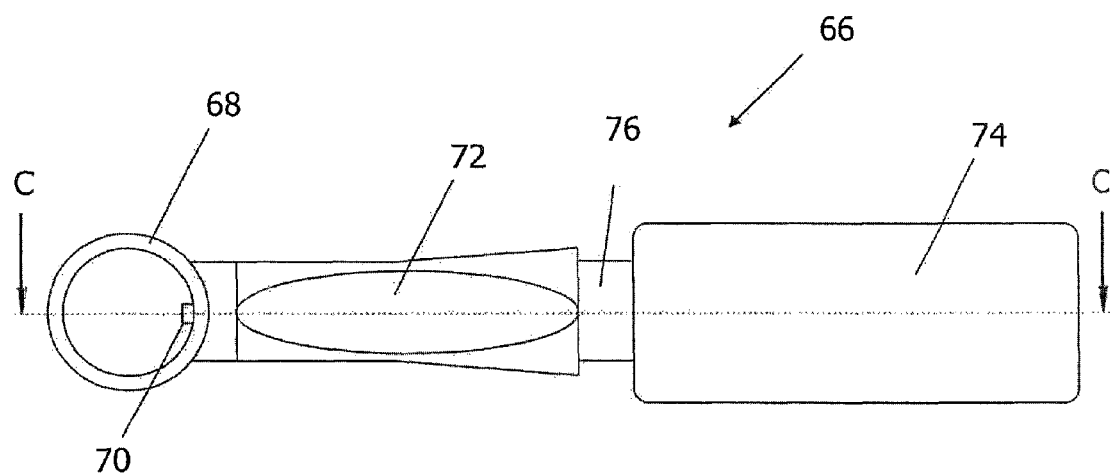
FIG. 13 shows a top view of an embodiment of a device for positioning the drill sleeve.
Figure 14:
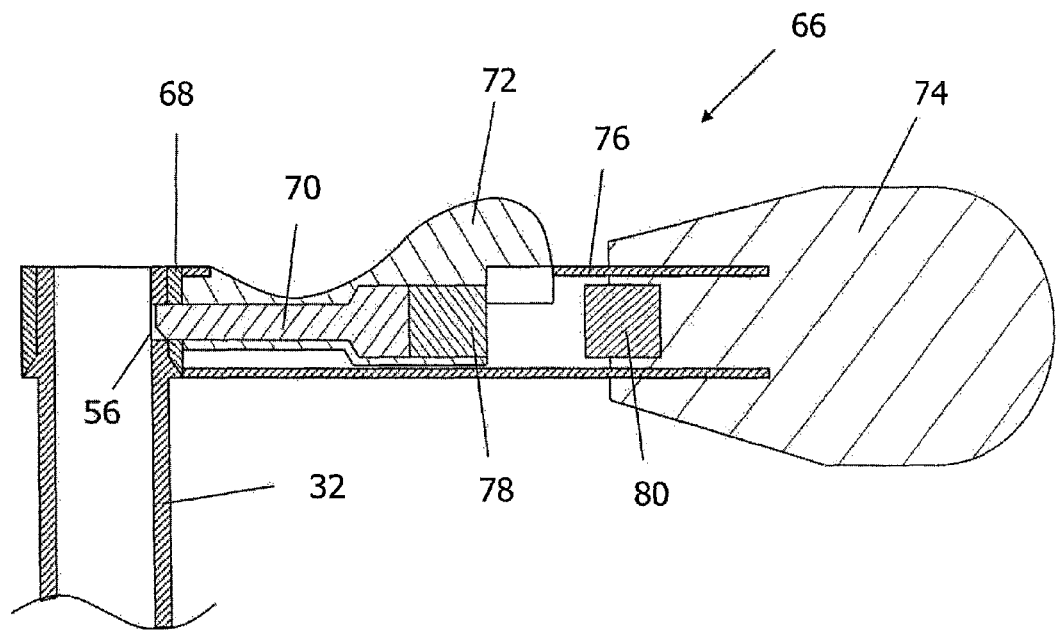
FIG. 14 shows a cross section of the positioning device along line C-C of FIG. 13, wherein the drill sleeve is connected to the positioning device.

FIGS. 13 and 14 show two views of a device 66 for positioning the drill sleeve 32. The positioning device 66 has a shaft 76, a handle 74 connected to one end of the shaft 76 and a sleeve holder 68 connected to the opposite end of the shaft 76. The sleeve holder 68 defines a space in which the drill sleeve 32 is to be inserted. A locking element 70 is movable along the shaft 76 and adapted to protrude into the space of the sleeve holder 68. A control portion 72 is connected to the locking element 70 for retracting the locking element 70 out from the space of the sleeve holder 68.

FIG. 14 shows a cross section of the positioning device 66 along line C-C of FIG. 13, wherein the drill sleeve 32 is connected to the positioning device 66. The device 66 comprises one magnet 78 connected to the end of the locking element 70 and one magnet 80 connected to the handle 74. The magnets 78, 80 face each other with a pole of the same type, and the locking element 70 is thereby magnetically forced to protrude (or "biased") into the space of the sleeve holder 68. A coil spring loaded locking element system could also be used. The front end of the locking element 70 engages with the recess 56 of the drill sleeve 32 to inhibit a rotational movement of the drill sleeve 32 relative to the positioning device 66.

Figure 15:
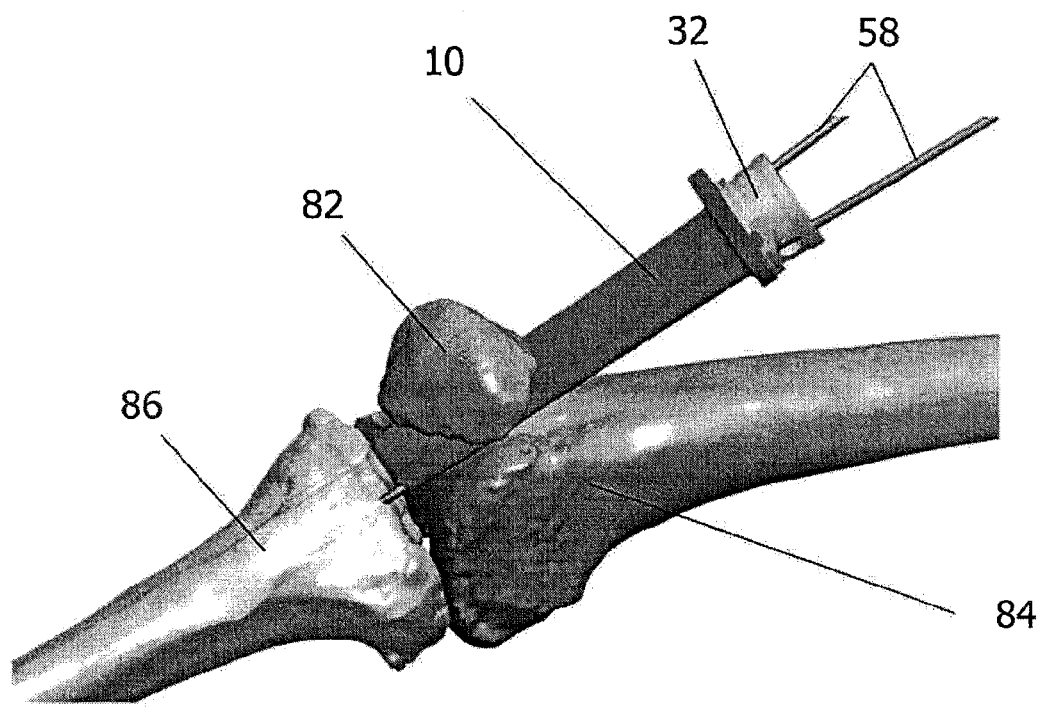
FIG. 15 shows a system embodiment used during suprapatellar surgery.

FIG. 15 shows a system comprising the sleeve 10 and the drill sleeve 32 during suprapatellar surgery. The drill sleeve 32 has been inserted into the sleeve 10. The positioning device 66, although not depicted in FIG. 15, could have been used to position the sleeve 10 and the drill sleeve 32 but might have been detached from the drill sleeve 32 after positioning.

In FIG. 15, a patella is denoted by 82, a femur is denoted by 84 and a tibia is denoted by 86. The sleeve 10 is inserted between the patella 82 and the femur 84 and reaches to the top of the tibia 86 (the tibial plateau). Two fixation elements 58, such as bone pins, are inserted through the openings 48 of the drill sleeve 32 and in the grooves 20 of the sleeve 10. Here, the grooves 20 are closed by the outer surface 40 of the drill sleeve 32 to define a closed canal that guides the fixation elements 58 into the tibia. The fixation elements 58 thus protrude into the tibia 86 for fixation of the system relative to the tibia 86.

Figure 16:
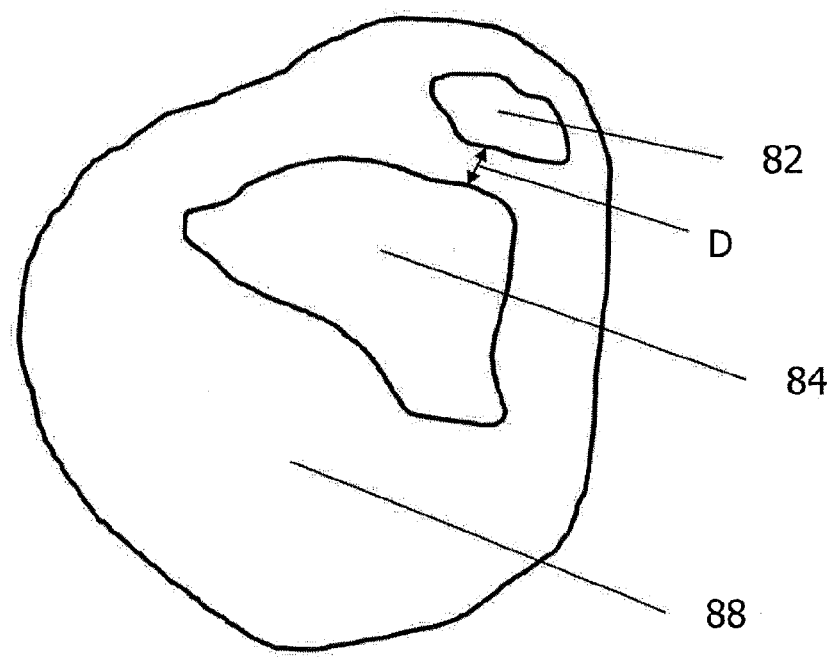
FIG. 16 shows a cross section of a leg at the patella in connection with suprapatellar surgery.

FIG. 16 shows a cross section of a leg at the patella 82. The remainder of the leg is denoted as 88. The distance between the patella 82 and the femur 84 is indicated by line D. During suprapatellar surgery, the sleeve 10 is inserted between the patella 82 and the femur 84 to access the tibia 86. If a sleeve 10 with two grooves 20 is used for suprapatellar surgery in this illustrated situation, the grooves 20 may be arranged more anteriorly along the circumference of the inner surface 16 of the sleeve 10. In other words, the angular distance between the grooves 20 may be less than 180° (e.g., 120° to 170°) and they may be arranged closer to the patella 82.

During suprapatellar surgery, a surgeon places the leg in extension or up to about 15° in flexion. The surgeon may insert the system comprising the trocar 60, the sleeve 10 and the drill sleeve 32 between the patella 82 and the femur 84 of the patient's leg and incise to the top of the tibia 86. Then a K-wire may be inserted through the central opening of the trocar 60 to achieve determination of the correct entry point. Due to the dimensions of the sleeve 10 in the direction D, the patella 82 does not have to be lifted up unnecessarily from the femur 84. Moreover, due to the flexible material of the sleeve 10 the associated joint is protected from being damaged when inserting the system. Alternately the trocar 60 can be inserted into sleeve 10, a guide wire inserted, the trocar 60 removed and then drill guide sleeve 32 inserted into sleeve 10 followed by drilling.

In a next step, two or more fixation elements 58 are inserted through the openings 48 of the drill sleeve 32 and in the grooves 20 of the sleeve 10. The openings 48 are aligned with the grooves 20 and thus function as aiming devices with respect to the grooves 20. The grooves 20 are closed, or covered, at their open ends by the outer surface of the drill sleeve 32, so that the fixation elements 58 upon insertion through the openings 48 are guided by the resulting laterally closed channels in the sleeve 10 towards the tibia 86. The fixation elements 58 are inserted into the tibia 86 for fixation of the system relative to the tibia 86. Subsequently, the trocar 60 is removed from the sleeve 10 and a drilling operation can be performed in the tibia 86 through the drill sleeve 32. Finally, a tibial implant such as an intramedullary nail is inserted into the tibia 86, and the system and the fixation elements 58 may be removed.

As has become apparent from the embodiments described with reference to FIGS. 1 to 16, the provision of at least two grooves at the inner surface of the sleeve enables a thinner overall system structure in the region of a joint to be bypassed during suprapatellar surgery. This results in a minimum incision to the joint surfaces and a minimum risk for injuries of the ligaments and tendons. Furthermore, the grooves at the inner surface of the sleeve facilitate cleaning and sterilization as they are open structures that can easily be accessed by a cleaning or sterilization medium.

While the present disclosure has been described with reference to exemplary embodiments, it will be appreciated that the present invention is not limited to what has been described above. For example, it will be appreciated that the dimensions of the parts may be varied as needed. Accordingly, it is intended that the present invention be limited only by the scope of the claims appended hereto.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system comprising:
   a tissue protection sleeve adapted for use in surgical procedures, the tissue protection sleeve having a longitudinal axis and comprising a first end, a second end, an inner surface, and an outer surface;
   wherein the tissue protection sleeve further comprises at least two grooves extending along the inner surface from the first end to the second end, wherein the grooves are adapted to accommodate elongated fixation elements, the grooves open to the sleeve inner surface;
   a drill sleeve adapted to be inserted into the tissue protection sleeve;
   wherein an outer surface of the drill sleeve closes the grooves of the tissue protection sleeve to define at least two closed canals adapted to receive and guide the elongated fixation elements;
   wherein the drill sleeve comprises a portion with an enlarged diameter at a first end of the drill sleeve;
   wherein the portion of the drill sleeve with an enlarged diameter comprises at least two openings at an end facing the second end of the drill sleeve, and wherein the at least two openings are axially aligned with the at least two closed canals of the sleeve when the drill sleeve is inserted into the tissue protection sleeve;
   whereby an elongated fixation element can be inserted into each of the closed canals through the respective opening; and
   wherein the tissue protection sleeve comprises an elastic material which permits bending of the tissue protection sleeve along the longitudinal axis.

2. The system according to claim 1, wherein the tissue protection sleeve has a portion along the longitudinal axis where the outer surface adjacent to the at least two grooves projects radially outwardly of the adjacent outer surface.

3. The system according to claim 1, wherein the grooves are substantially parallel with the longitudinal axis of the sleeve.

4. The system according to claim 1, wherein the two grooves are located substantially at opposite sides along a circumference of the inner surface.

5. The system according to claim 1, wherein the angular distance between the two grooves along a circumference of the inner surface is less than 180°.

6. The system according to claim 1, wherein the tissue protection sleeve further comprises a gripping flange portion radially and outwardly from the first end of the sleeve.

7. The system according to claim 1, wherein the at least two openings in the drill sleeve are inclined relative to the longitudinal axis of the drill sleeve.

8. The system according to claim 7, wherein the tissue protection sleeve and the drill sleeve are rotationally locked relative to each other.

9. The system according to claim 8, wherein the drill sleeve comprises a recess at the circumference of the portion with an enlarged diameter.

10. The system according to claim 9, wherein the system further comprises at least two fixation elements adapted to be inserted in the grooves.

11. The system according to claim 10, wherein the system further comprises a device adapted to engage and to position at least one of the sleeve and the drill sleeve with respect to the tibia.

12. The system according to claim 1, wherein the system further comprises a trocar adapted to be inserted into the drill sleeve.

13. A method for suprapatellar surgery, comprising: providing a system comprising;
   a tissue protection sleeve adapted for use in surgical procedures, the tissue protection sleeve having a longitudinal axis and comprising a first end, a second end, an inner surface, and an outer surface;
   wherein the tissue protection sleeve further comprises at least two grooves extending along the inner surface from the first end to the second end, wherein the grooves are adapted to accommodate elongated fixation elements, the grooves open to the sleeve inner surface;
   a drill sleeve adapted to be inserted into the tissue protection sleeve;
   a trocar adapted to be inserted into the drill sleeve;
   wherein an outer surface of the drill sleeve closes the grooves of the tissue protection sleeve to define at least two closed canals adapted to receive and guide the elongated fixation elements;
   wherein the drill sleeve comprises a portion with an enlarged diameter at a first end of the drill sleeve;
   wherein the portion of the drill sleeve with an enlarged diameter comprises at least two openings at an end facing the second end of the drill sleeve, and wherein the at least two openings are axially aligned with the at least two closed canals of the sleeve when the drill sleeve is inserted into the tissue protection sleeve;
   whereby an elongated fixation element can be inserted into each of the closed canals through the respective opening;
   inserting at least two fixation elements into the tibia through a respective one of the at least two openings of the drill sleeve enlarged portion and the respective grooves of the tissue protection sleeve;
   inserting a drill guide sleeve into the tissue protection sleeve;
   inserting a trocar into the tissue protection sleeve;
   inserting a guide wire into a tibia through the trocar;
   thereafter removing the trocar;
   drilling a bore in the tibia using the drill sleeve as a guide; and
   thereafter inserting a bone nail in the drilled tibia.

14. The method as set forth in claim 13 wherein the trocar is inserted into the drill sleeve.

15. A system comprising:
   a tissue protection sleeve adapted for use in surgical procedures, the tissue protection sleeve having a central longitudinal axis and comprising a first end, a second end, an inner surface, and an outer surface;
   wherein the tissue protective sleeve further comprises at least two grooves extending along the inner surface from the first end to the second end, wherein the grooves are adapted to accommodate elongated fixation elements, the grooves open to the sleeve inner surface;
   a drill sleeve having a central longitudinal axis adapted to be inserted into the tissue protection sleeve;
   wherein an outer surface of the drill sleeve closes the grooves of the tissue protection sleeve to define at least two closed canals adapted to receive and guide the elongated fixation elements;
   wherein the drill sleeve comprises a portion with an enlarged diameter at a first end of the drill sleeve;
   wherein the portion of the drill sleeve with an enlarged diameter comprises at least two openings at an end facing the second end of the drill sleeve, and wherein the at least two openings are axially aligned with the at least two closed canals of the sleeve when the drill sleeve is inserted into the tissue protection sleeve, wherein the at least two openings of the drill sleeve and the two grooves of the tissue protection sleeve are angled towards their respective central longitudinal axis; and whereby an elongated fixation element can be inserted into each of the closed canals through the respective opening.

16. A system comprising:

a flexible tissue protection sleeve adapted for use in surgical procedures, the flexible tissue protection sleeve having a central longitudinal axis and comprising a first end, a second end, an inner surface, and an outer surface, the flexible sleeve second end capable of flexing from a first configuration with a first orientation of the central longitudinal axis to a second configuration with a second orientation of the central longitudinal axis different than the first orientation;

wherein the flexible tissue protective sleeve further comprises at least two grooves extending along the inner surface from the first end to the second end, wherein the grooves are adapted to accommodate elongated fixation elements, the grooves open to the sleeve inner surface;

a drill sleeve adapted to be inserted into the tissue protection sleeve;

wherein an outer surface of the drill sleeve closes the grooves of the tissue protection sleeve to define at least two closed canals adapted to receive and guide the elongated fixation elements;

wherein the drill sleeve comprises a portion with an enlarged diameter at a first end of the drill sleeve;

wherein the portion of the drill sleeve with an enlarged diameter comprises at least two openings at an end facing the second end of the drill sleeve, and wherein the at least two openings are axially aligned with the at least two closed canals of the sleeve when the drill sleeve is inserted into the tissue protection sleeve; and whereby an elongated fixation element can be inserted into each of the closed canals through the respective opening.

* * * * *